United States Patent [19]

Lovgren et al.

[11] Patent Number: 4,853,230

[45] Date of Patent: * Aug. 1, 1989

[54] PHARMACEUTICAL FORMULATIONS OF ACID LABILE SUBSTANCES FOR ORAL USE

[75] Inventors: Kurt I. Lovgren, Mölnlycke; Ake G. Pilbrant, Kungsbacka, both of Sweden; Mitsuru Yasumura; Satoshi Morigaki, both of Hyogo; Minoru Oda, Ohita; Naohiro Ohishi, Fukuoka, all of Japan

[73] Assignee: Aktiebolaget Hassle, Molndal, Sweden

[ * ] Notice: The portion of the term of this patent subsequent to Nov. 22, 2005 has been disclaimed.

[21] Appl. No.: 40,490

[22] Filed: Apr. 20, 1987

[30] Foreign Application Priority Data

Apr. 30, 1986 [GB] United Kingdom ................ 8610573

[51] Int. Cl.[4] .............................................. A61K 9/46
[52] U.S. Cl. ..................... 424/466; 424/468; 424/475; 424/479; 424/480; 424/482; 424/456
[58] Field of Search ............... 424/470, 495, 468, 480, 424/482, 466, 471, 472

[56] References Cited

U.S. PATENT DOCUMENTS

| | | | |
|---|---|---|---|
| 2,540,979 | 2/1951 | Clymer et al. | 167/82 |
| 3,131,123 | 4/1964 | Masquelier | 424/466 |
| 4,685,918 | 8/1987 | Amidon et al. | 604/892 |
| 4,786,505 | 11/1988 | Lovgren et al. | 424/468 |

FOREIGN PATENT DOCUMENTS

| | | |
|---|---|---|
| 0005129 | 6/1981 | European Pat. Off. . |
| 0077956 | 5/1983 | European Pat. Off. ............ 424/495 |
| WO85/03436 | 8/1985 | PCT Int'l Appl. . |
| 0862376 | 3/1961 | United Kingdom ................ 424/470 |
| 1485676 | 3/1982 | United Kingdom . |

OTHER PUBLICATIONS

Pilbrant, A and Cederberg, C, "Development of an Oral Formulation of Omeprazole," Scand. J. Gastroenterology, 1985, pp. 113–120.

Blanchi, A. et al., "Control of Acute Zollinger-Ellison Syndrome with Intravenous Omeprazole", The Lancet, Nov. 27, 1982, pp. 1223–1224.

Primary Examiner—Thurman K. Page
Attorney, Agent, or Firm—Brumbaugh, Graves, Donohue & Raymond

[57] ABSTRACT

Pharmaceutical preparation containing an acid labile compound together with an alkaline reacting compound or an alkaline salt of an acid labile compound optionally together with an alkaline compound as the core material, one or more subcoating layers comprising inert reacting compounds which are soluble or rapidly disintegrating in water, or polymeric, water soluble filmforming compounds, optionally containing pH-buffering alkaline compounds and an enteric coating as well as a process for the preparation thereof and the use in the treatment of gastrointestinal diseases.

15 Claims, No Drawings

PHARMACEUTICAL FORMULATIONS OF ACID LABILE SUBSTANCES FOR ORAL USE

FIELD OF THE INVENTION

The present invention is related to new pharmaceutical preparations containing acid labile substances for oral use, to a method for the manufacture of such preparations and to a method of affecting gastric acid secretion and providing gastrointestinal cytoprotective effect when using them.

BACKGROUND OF THE INVENTION

Acid labile substances present a problem to the formulator when formulating a pharmaceutical dosage form for oral use. In order to prevent the substances from contact with the acid reacting gastric juice after oral intake, the conventional way to solve this problem is to coat the dosage form with an enteric coating. The coating is a group of substances/polymers with the common feature of being practically insoluble in acid media, while they are soluble in neutral to alkaline media. For substances that are labile in acid media, but have better stability in neutralto alkaline media, it is often advantageous to add alkaline reacting inactive constituents in order to increase the stability of the active compound during manufacture and storage.

A group of comounds exerting these stability properties are substituted benzimidazoles with the geneal formula I

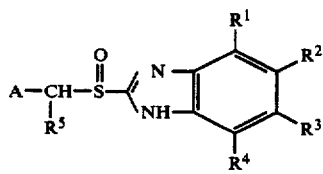

wherein A is an optionally substituted heterocyclic group and $R^1$, $R^2$, $R^3$, and $R^4$ are the same or different as defined below and $R^5$ is H or a lower alkyl, or the compound 2-[(2-dimethylaminobenzyl)sulfinyl]-benzimidazole.

The compounds with the general formula I are virtually biologically inactive as such, but degrade/transform to active inhibitors of certain enzyme systems in acid media.

As examples of compounds with the mentioned properties the compounds described in the patents U.S. Pat. No. 4045 563, EP-1-0 005 129 and BE-898 880 and the patent applications EP-85850258,6, EP-A1-0 080 602, EP-0127 736, EP-0 134 400, EP-0 130 729, EP-0 150 586, DE-3415971 GB-2 082 580 and SE-A-8504048-3 may be mentioned. The last application describes 2-(2-disubstituted-aminobenzyl)sulfinyl benzimidazoles, e.g. 2-(2-dimethylaminobenzyl)sulfinyl benzimidazole, also called, NC-1300 and presented by Prof. S. Okabe at the Symposium on Drug Activity held on Oct. 17, 1985 in Nagoya, Japan, and which interacts with the H+K+-ATPase after acid degradation within the parietal cells. (See for instance B. Wallmark, A. Brändstroöm and H. Larson "Evidence for acid-induced transformation of omeprazole into an active inhibitor of H+K+-ATPase within the partial cell", Biochemica et Biophysica Acta 778, 549–558, 1984). Other compounds with similar properties are further mentioned in the patent U.S. Pat. No. 4 182 766 and the patent applications GB-2 141 429, EP-O 146 370 and GB-2 082 580. A common feature of these compounds are that they are transformed into the biologically active compounds via rapid degradation/transformation in acid media.

The stability profile of some compounds with the general formula I above is exemplifide in the Table 1 below, where the half-life of the degradation/transformation reaction in solution at pH 2 and 7 are given.

TABLE 1

Rate of degradation/transformation of compounds with the general structure

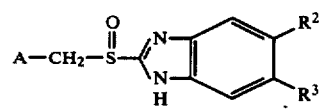

| Compound No | A | $R^2$ $R^3$ | Half-life (mintues) for the transformation to the active moiety at pH = 2 | at pH = 7 |
|---|---|---|---|---|
| 1. | ![3-CH3,2-CH3 pyridine] | 5-COOCH₃;6-CH₃ | 11 | 150 |
| 2. | ![3,5-diCH3 pyridine] | 5-CH₃;H | 5.4 | 1700 |
| 3. | ![3-OCH3 pyridine] | 5-CF₃;H | 1.9 | 122 |

TABLE 1-continued

Rate of degradation/transformation of compounds with the general structure $$A-CH_2-S(=O)-\text{[benzimidazole]}-R^2, R^3$$

| Compound No | A | $R^2$ $R^3$ | Half-life (minutes) for the transformation to the active moiety | |
|---|---|---|---|---|
| | | | at pH = 2 | at pH = 7 |
| 4. | 4-OCH$_3$, 3-CH$_3$ pyridine | 5-CF$_3$;H | 2.0 | 8.8 |
| 5. | 3-C$_2$H$_5$, 4-phenoxy pyridine | 5-OCH$_3$;H | 3.7 | 1620 |
| 6. | 4-phenoxy, 2-methyl pyridine | 5-OCH$_3$;H | 4.0 | 3900 |
| 7. | N-CH$_3$ benzimidazole | 5-C$_2$H$_5$;H | 33 | not determined |

Substituted sulfoxides, such as for instance the substituted benzimidazoles described in EP-1-0005129 are potent inhibitors of gastric acid secretion. The substituted benzimidazoles are susceptible to degradation/transformation in acid reacting and neutral media.

It is an inherent property of these compounds to be activated to the active moiety in the acid environment within the parietal cells. The activated compound interacts with the enzyme in the parietal cells, which mediates the production of hydrochloric acid in the gastric mucosa. All compounds of the class of substituted benzimidazoles, containing a sulfoxide grouping, which interferes with the H+K+-ATPase in the parietal cells hitherto known are all also degraded in acid media.

A pharmaceutical dosage form of acid labile substances, which prevents the substances from contact with acidic gastric juice, must be enteric coated. Ordinary enteric coatings, however, are made of acidic compounds. If covered with such a conventional enteric coating, the acid labile substance rapidly decomposes by direct or indirect contact with it, with the result that the preparations become badly discoloured and lose in content of the active compound with the passage of time.

In order to enhance the storage stability, the cores which contain the acid labile substance must also contain alkaline reacting constituents. When such an alkaline core is enteric coated with an amount of a conventional enteric coating polymer such as, for example, cellulose acetate phthalate, that permits the dissolution of the coating and the active drug contained in the cores in the proximal part of the small intestine, it also will allow some diffusion of water or gastric juice through the enteric coating into the cores, during the time the dosage form resides in the stomach before it is emptied into the small intestine. The diffused water or gastric juice will dissolve parts of the core in the close proximity of the enteric coating layer and there form an alkaline solution inside the coateddosage form. The alkaline solution will interfere with the enteric coating and eventually dissolve it.

In DE-A1-3 046 559 a way to coat a dosage form is described. First the dosage form is coated with a water insoluble layer containing microcrystalline cellulose and then with a second enteric coating with the aim to achieve a dosage form which releases the active drug in the colon. This method of preparation will not give the desired release of the compounds with the general formula I above in the small intestine.

U.S. Pat. No. 2 540 979 describes an enteric coated oral dosage form, where the enteric coating is combined with a second and/or first coating of a water insoluble "wax" layer. This method of preparation is not applicable on cores containing a compound with the general formula I since direct contact between substances such as cellulose acetate phthalate (CAP) and a compound of formula I causes degradation and discolouration of the compounds of the formula I.

DE-B2-23 36 218 describes a method to produce a dialysis membrane consisting of a mixture of one or more conventional enteric coating polymers and one or more insoluble cellulose derivatives. Such a membrane will not give a proper protection of the acid labile compounds of the formula I in gastric juice.

DE-A1-1 204 363 describes a three-layer coating procedure. The first layer is soluble in gastric but is insoluble in intestinal juice. The second is water soluble regardless of pH and the third layer is an enteric coating. This preparation as well as the preparation described in DE-A1-1 617 615 result in a dosage form which is not dissolved in gastric juice and which only dissolves slowly in intestinal juice. Such preparations cannot be used for the compounds of the formula I, where a rapid release of the drug in the small intestine is needed. DE-A1 12 04 363 describes coating with three layers to achieve release of a drug in the ileum, an aim which is outside the scope of the present invention. GB-A-1 485 676 describes a way to obtain a preparation which effervesces in the small intestine. This is obtained by the enteric coating of a core containing the active drug and an effervescing system such as a combination of carbonate and/or bicarbonate salt and a pharmaceutically acceptable acid. This formulation cannot be adopted for a pharmaceutical dosage form containing a compound of formula I as the presence of an acid in contact with a compound of formula I in the cores would give as a result that the compound of formula I was degraded.

WO No. 85/03436 describes a pharmaceutical preparation, wherein cores containing active drugs mixed with for instance buffering components such as sodium dihydrogenphosphate with the aim of maintaining a constant pH and a constant rate of diffusion, are coated with a first coating which controls as the diffusion. This formulation cannot be adopted for acid labile compounds where a rapid release in the small intestive is wanted. Direct application of an enteric coating onto the cores would also adversely influence the storage stability of such dosage forms containing acid labile compounds.

Outline of the invention

According to the present invention it has been found that the known acid labile compounds with the general formula I above in which $R^1$, $R^2$, $R^3$ and $R^4$ are the same or different and are

| | | |
|---|---|---|
| (a) | hydrogen | |
| (b) | halogen, e.g. F, Cl, Br, I | |
| (c) | —CN | |
| (d) | —CHO | |
| (e) | —CF$_3$ | |
| (f) | $\begin{array}{c} O \\ \parallel \\ -C-R^{11} \end{array}$ | |
| (g) | —O—C—R$^{12}$ | |
| (h) | —CH(OR$^{13}$)$_2$ | |
| (i) | —(Z)$_n$—B—D | |
| (j) | aryl containing up to 10 carbon atoms | |
| (k) | aryloxy containing up to 10 carbon atoms, optionally substituted by alkyl containing 1-6 carbon atoms | |

-continued

| | |
|---|---|
| (l) | -alkylthio containing 1-6 carbon atoms |
| (m) | —NO$_2$ |
| (n) | -alkylsulfinyl containing 1-6 carbon atoms |
| (o) | or wherein adjacent groups R$^1$, R$^2$, R$^3$ and R$^4$ together with the adjacent carbon atoms in the benzimidazole ring form a 5-, 6-, 7-membered monocyclic ring or a 9-, 10- or 11-membered bicyclic ring, which rings may be saturated or unsaturated and may contain 0-3 hetero atoms selected from —N— and —O—, and which rings may be optionally substituted with 1-4 substituents selected from alkyl groups with 1-3 carbon atoms, alkylene radicals containing 4-5 carbon atoms giving spiro compounds, or two or four of these substituents together form one or two oxo groups $\begin{array}{c} O \\ \parallel \\ (-C-) \end{array}$, whereby if R$^1$ and R$^2$, R$^2$ and R$^3$ or R$^3$ and R$^4$ together with the adjacent carbon atoms in the benzimidazole ring form two rings they may be condensed with each other, in which formulas R$^{11}$ and R$^{12}$, which are the same or different, are |
| (a) | aryl containing up to 10 carbon atoms |
| (b) | alkoxy containing 1-4 carbon atoms |
| (c) | alkoxyalkoxy containing 1-3 carbon atoms in each alkoxy part |
| (d) | arylalkoxy containing 1-2 carbon atoms in the alkoxy part and up to 10 carbon atoms in the aryl part |
| (e) | aryloxy containing up to 10 carbon atoms |
| (f) | dialkylamino containing 1-3 carbon atoms in the alkyl parts, or |
| (g) | pyrrolidino or piperidino, optionally substituted with alkyl containing 1-3 carbon atoms; |

R$^{13}$ is
(a) alkyl containing 1-4 carbon atoms, or
(b) alkylene containing 2-3 carbon atoms;

Z is $\begin{array}{c} O \\ \parallel \\ -O- \text{ or } -C-; \end{array}$ n is 0 or 1;

B is
(a) alkylene containing 1-6 carbon atoms
(b) cycloalkylene containing 3-6 carbon atoms
(c) alkenylene containing 2-6 carbon atoms
(d) cycloalkylene containing 3-6 carbon atoms, or
(e) alkynylene containing 2-6 carbon atoms;

D is
(a) H
(b) —CN
(c) $\begin{array}{c} O \\ \parallel \\ -C-R^9 \end{array}$
(d) $\begin{array}{c} O \\ \parallel \\ -(Y)_m-(C)_r-R^{10} \end{array}$ wherein R$^9$ is
(a) alkoxy containing 1-5 carbon atoms, or
(b) dialkylamino containing 1-3 carbon atoms in the alkyl parts;

m is 0 or 1;
r is 0 or 1;

Y is
(a) —O—
(b) —NH—
(c) —NR$^{10}$—;

R$^{10}$ is
(a) H
(b) alkyl containing 1-3 carbon atoms
(c) arylalkyl containing 1-2 carbon atoms in the alkyl part and up to 10 carbon atoms in the aryl part
(d) aryl containing up to 10 carbon atoms;

R$^5$ is H, CH$_3$ or C$_2$H$_5$;

-continued

A is especially a pyridyl group in which $R^6$ and $R^8$ are the same or different, are

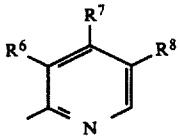

| | (a) | H or |
| --- | --- | --- |
| | (b) | alkyl containing 1-6 carbon atoms; |
| $R^7$ is | (a) | H |
| | (b) | alkyl containing 1-8 carbon atoms |
| | (c) | alkoxy containing 1-8 carbon atoms |
| | (d) | alkenyloxy containing 2-5 carbon atoms |
| | (e) | alkynyloxy containing 2-5 carbon atoms |
| | (f) | alkoxyalkoxy containing 1-2 carbon atoms in each alkoxy group |
| | (g) | aryl containing up to 10 carbon atoms |
| | (h) | arylalkyl containing 1-6 carbon atoms in the alkyl part and up to 10 carbon atoms in the aryl part |
| | (i) | aryloxy containing up to 10 carbon atoms, optionally substituted by alkyl containing 1-6 carbon atoms |
| | (j) | arylalkoxy containing 1-6 carbon atoms in the alkoxy part and up to 10 carbon atoms in the aryl part |
| | (k) | dialkylaminoalkoxy containing 1-2 carbon atoms in the alkyl substituents on the amino nitrogen and 1-4 carbon atoms in the alkoxy group |
| | (l) | oxacycloalkyl containing one oxygen atom and 3-7 carbon atoms |
| | (m) | oxacycloalkoxy containing two oxygen atoms and 4-7 carbon atoms |
| | (n) | oxacycloalkylalkyl containing one oxygen atom and 4-7 carbon atoms |
| | (o) | oxacycloalkylalkoxy containing two oxygen atoms and 4-6 carbon atoms, or |
| | (p) | $R^6 R^7$, or $R^7$ and $R^8$ together with the adjacent carbon atoms in the pyridine ring form a ring wherein the part constituted by $R^6$ and $R^7$, or $R^7$ and $R^8$, is<br>—CH=CH—CH=CH—<br>—O—(CH$_2$)$_p$—<br>—S—(CH$_2$)$_v$—<br>—CH$_2$(CH$_2$)$_p$—<br>—O—CH=CH—<br>—NH—CH=CH—<br>—N—CH=CH—<br>     │<br>    CH$_3$ | wherein p is 2, 3 or 4, v is 2 or 3 and the O and N atoms always are attached to position 4 in the pyridine ring; provided that not more than one of $R^6$, $R^7$ and $R^8$ is hydrogen can be formulated into an enteric coated dosage form.

The object of the present invention is thus an enteric coated dosage form of acid labile compounds with the general formula I defined above except the compound omeprazole, 5-methoxy-2-(4-methoxy-3,5dimethyl-2-pyridinyl)methyl sulfinyl-1H-benzimidazole. Another compound, which may be enteric coated according to the invention is 2-(2-dimethylaminobenzyl)sulfinyl-benzimidazole. The new preparations are resistant to dissolution in acid media, dissolve rapidly in neutral to alkaline media and have a good stability during long-term storage. The new dosage form is characterized in the following way. Cores containing the acid labile compound mixed with alkaline compounds or an alkaline salt of the acid labile compound optionally mixed with an alkaline compound are coated with two or more layers, whereby the first layer/layers is/are soluble in water or rapidly disintegrating in water and consist(s) of non-acidic, otherwise inert pharmaceutically acceptable substances. This/these first layer/layers separates/separate the alkaline core material from the outer layer, which is an enteric coating. The final, enteric coated dosage form is treated in a suitable way to reduce the water content to a very low level in order to obtain a good stability of the dosage form during long-term storage.

As examples of compounds especially suitable for the pharmaceutical dosage form according to the invention the compounds listed in Table 1 can be mentioned.

The half-life of degradation of the compounds 1-6 in Table 1 in water solution at pH-values less than four is in most cases shorter than ten minutes. Also at neutral pH-values the degradation reaction proceeds rapidly, e.g. at pH=7 the half-life of degradation is between 10 minutes and 65 hours while at higher pH-values the stability in solution for most compounds is much better. The stability profile is similar in solid phase. The degradation is catalyzed by acid reacting substances. The acid labile compounds are stabilized in mixtures with alkaline reacting substances.

From what is said about the stability properties of the acid labile compounds listed above it is obvious that an oral dosage form of the said compounds must be protected from contact with the acid reacting gastric juice in order to reach the small intestine without degradation.

DETAILED DESCRIPTION OF THE INVENTION

Cores

The acid labile active compound is mixed with inert, preferably water soluble, conventional pharmaceutical constituents to obtain the preferred concentration of the active compound in the final mixture and with an alkaline reacting, otherwise inert, pharmaceutically acceptable substance (or substances), which creates a "micro-pH" around each particle of active compound of not less than pH=7, preferably not less than pH=8, when water is adsorbed to the particles of the mixture or when water is added in small amounts to the mixture. Such substances can be chosen among, but are not restricted to substances such as the sodium, potassium, calcium, magnesium and aluminium salts of phosphoric acid, carbonic acid, citric acid or other suitable weak inorganic or organic acids; substances normally used in antacid preparations such as aluminium, calcium and magnesium hydroxides; magnesium oxide or composite substances such as Al$_2$O$_3$.6MgO CO$_2$.12H$_2$O, (Mg$_6$Al$_2$-(OH)$_{16}$CO$_3$4H$_2$O), MgO.Al$_2$O$_3$.2SiO$_2$.nH$_2$O, wherein n not is an integer and less than 2 or similar compounds; organic pH-buffering substances such as trishydroxy-methylaminomethane or other similar, pharmaceutically acceptable pH-buffering substances. The stabilizing, high pH-value in the powder mixture can also be achieved by using an alkaline reacting, salt of the active compound such as the sodium, potassium, magnesium, calcium etc. salts of acid labile compounds, either alone or in combination with a conventional buffering substance as previously described.

The powder mixture is then formulated into small beads i.e. pellets or tablets, by conventional pharmaceutical procedures. The pellets, tablets or gelatin capsules are used as cores for further processing.

Separating layer

The alkaline reacting cores containing an acid labile compound must be separated from the enteric coating polymer(s) containing free carboxyl groups, which otherwise causes degradation/discolouration of the acid labile compound during the coating process of during storage. The subcoating layer, (the separating layer), also serves as a pH-buffering zone in which hydrogen ions diffusing from the outside in towards the alkaline core can react with hydroxyl ions diffusing from the alkaline core towards the surface of the coated articles. The pH-buffering properties of the separating layer can be further strengthened by introducing in the layer substances chosen from a group of compounds usually used in antacid formulations such as, for instance, magnesium oxide, hydroxide or carbonate, aluminium or calcium hydroxide, carbonate or silicate; composite aluminium/magnesium compounds such as, for instance $Al_2O_3.6MgO\ CO_2.12H_2O$, $(Mg_6Al_2(OH)_{16}CO_3, 4H_2O)$, $MgO.Al_2O_3.2SiO_2.nH_2O$, wherein n not is an integer and less than 2 or similar compounds; or other pharmaceutically acceptable pH-buffering substances such as, for instance the sodium, potassium, calcium, magnesium and aluminium salts of phosphoric, citric or other suitable, weak, inorganic or organic acids.

The separating layer consists of one or more water soluble inert layers, optionally containing pH-buffering substances.

The separating layer(s) can be applied to the cores—pellets or tablets—by conventional coating procedures in a suitable coating pan or in a fluidized bed apparatus using water and/or conventional organic solvents for the coating solution. The material for the separating layer is chosen among the pharmaceutically acceptable, water soluble, inert compounds or polymers used for film-coating applications such as, for instance sugar, polyethylene glycol, polyvinylpyrrollidone, polyvinyl alcohol, hydroxypropyl cellulose, hydroxymethyl cellulose, hydroxypropyl methylcellulose or the like. The thickness of the separating layer is not less than 2 $\mu m$, for small spherical pellets preferably not less than 4 $\mu m$, for tablets preferably not less than 10 $\mu m$.

In the case of tablets another method to apply the coating can be performed by the drycoating technique. First a tablet containing the acid labile compound is compressed as described above. Around this tablet another layer is compressed using a suitable tableting machine. The outer, separating layer, consists of pharmaceutically acceptable, in water soluble or in water rapidly disintegrating tablet excipients. The separating layer has a thickness of not less than 1 mm. Ordinary plasticizers, pigments, titanium dioxide talc and other additives may also be included into the separating layer.

In the case of gelatin capsules the gelatin capsule itself serves as separating layer.

Enteric coating layer

The enteric coating layer is applied on to the subcoated cores by conventional coating techniques such as, for instance, pan coating or fluidized bed coating using solutions of polymers in water and/or suitable organic solvents or by using latex suspensions of said polymers. As enteric coating polymers can be used, for example, cellulose acetate phthalate, hydroxypropyl methylcellulose phthalate, polyvinyl acetate phthalate, co-polymerized methacrylic acid/methacrylic acid methyl esters such as, for instance, compounds known under the trade name Eudragit ® L 12,5 or Eudragit ® L 100, (Röhm Pharma) or similar compounds used to obtain enteric coatings.

The enteric coating can also be applied using water-based polymer dispersions, e.g. Aquateric (FMC Corporation), Eudragit ® L 100-55 (Röhm Pharma), Coating CE 5142 (BASF). The enteric coating layer can optionally contain a pharmaceutically acceptable plasticizer such as, for instance, cetanol, triacetin, citric acid esters such as, for instance, those known under the trade name Citroflex ® (Pfizer) phthalic acid esters, dibutyl succinate or similar plasticizers.

The amount of plasticizer is usually optimized for each enteric coating polymer(s) and is usually in the range of 1-20% of the enteric coating polymer(s). Dispersants such as talc, colourants and pigments may also be included into the enteric coating layer.

Thus the special preparation according to the invention consists of cores containing the acid labile compound mixed with an alkaline reacting compound or cores containing an alkaline salt of the acid labile compound optionally mixed with an alkaline reacting compound. The cores suspended in water forms a solution or a suspension which has a pH, which is higher than that of a solution in which the polymer used for enteric coating is just soluble. The cores are coated with a water soluble or in water rapidly disintegrating coating, optionally containing a pH-buffering substance, which separates the alkaline cores from the enteric coating. Without this separating layer the resistance towards gastric juice would be too short and the storage stability of the dosage form would be unacceptably short. The sub-coated dosage form is finally coated with an enteric coating rendering the dosage form insoluble in acid media, but rapidly disintegrating/dissolving in netural to alkaline media such as, for instance the liquids present in the proximal part of the small intestine, the site where dissolution is wanted.

Final dosage form

The final dosage form is either an enteric coated tablet or capsule or in the case of enteric coated pellets, pellets dispensed in hard gelatin capsules or sachets or pellets formulated into tablets. It is essential for the long term stability during storage that the water content of the final dosage form containing acid labile compound (enteric coated tablets, capsules or pellets) is kept low, preferably not exceeding 1.5% by weight.

Process

A process for the manufacture of the oral dosage form represents a further aspect of the invention. After the forming of the cores the cores are first coated with the separating layer and then with the enteric coating layer. The coating is carried out as described above.

The preparation according to the invention is especially advantageous in reducing gastric acid secretion and/or providing a gastrointestinal cytoprotective effect. It is usually administered one to several times a day. The typical daily dose of the active substance varies and will depend on various factors such as for example the individual requirement of the patients, the mode of administration and the disease. In general the dosage will be in the range of 1 to 400 mg per day of active substance. A method for the treatment of such conditions using the vovel oral dosage form represents a further aspect of the invention.

The invention is described in detail in the following examples:

EXAMPLES

Examples 1-3 exemplify the invention.

EXAMPLE 1

| Uncoated pellets | | |
|---|---|---|
| I | Lactose powder | 253 g |
| | Lactose anhydrous | 167 g |
| | Hydroxypropyl cellulose | 25 g |
| II | Compound 1, Table I | 50 g |
| | Sodium lauryl sulphate | 5 g |
| | Disodium hydrogen phosphate | 1.5 g |
| | Sodium dihydrogen phosphate | 0.1 g |
| | Distilled water | 125 g |

The dry ingredients (I) were premixed in a mixer. Addition of a granulation liquid (II) containing the suspended active compound was made and the mass was wet-mixed to a proper consistency. The wet mass was pressed through an extruder and spheronized to pellets. The pellets were dried and classified into suitable particle size ranges.

| Subcoated pellets | | |
|---|---|---|
| | Uncoated pellets | 500 g |
| III | Hydroxypropyl methyl-cellulose | 20 g |
| | Distilled water | 400 g |

The polymer solution (III) was sprayed onto the uncoated pellets in a fluidized bed apparatus. The spray guns were placed above the fluidized bed.

| Enteric coated pellets | | |
|---|---|---|
| | Subcoated pellets | 500 g |
| IV | Hydroxypropyl methylcellulose phthalate | 57 g |
| | Cetyl alcohol | 3 g |
| | Acetone | 540 g |
| | Ethanol | 231 g |

The polymer solution (IV) was sprayed on the subcoated pellets in a fluidized bed apparatus with spray guns placed above the bed. After drying to a water content of 0.5% the enteric coated pellets were classified and filled into hard gelatin capsules in an amount of 284 mg, corresponding to 25 mg of active compound 1. 30 capsules were packed in tight containers together with a desiccant.

EXAMPLE 2

Formulation with the sodium salt of compound 2 according to Table I.

| Uncoated pellets | | |
|---|---|---|
| I | Compound 2, Table I sodium salt | 339 g |
| | Mannitol powder | 2 422 g |
| | Lactose anhydrous | 120 g |
| | Hydroxypropyl cellulose | 90 g |
| | Microcrystalline cellulose | 60 g |
| II | Sodium lauryl sulphate | 7 g |
| | Distilled water | 650 g |

The preparation was made as described in Example 1 with the exception that the sodium salt of compound 2 was added together with the other ingredients in mixture I.

| Subcoated pellets | | |
|---|---|---|
| | Uncoated pellets | 500 g |
| III | Hydroxypropyl methylcellulose | 20 g |
| | Aluminium hydroxide/magnesium carbonate | 4 g |
| | Distilled water | 400 g |
| | Pellets subcoated with III | 500 g |
| IV | Hydroxypropyl methylcellulose | 20 g |
| | Distilled water | 400 g |

The two subcoat layers, III and IV, were applied to the uncoated pellets in a fluidized bed apparatus in consecutive order as previously described.

| Enteric coated pellets | | |
|---|---|---|
| | Subcoated pellets | 500 g |
| V | Hydroxypropyl methylcellulose phthalate | 57 g |
| | Cetyl alcohol | 3 g |
| | Acetone | 540 g |
| | Ethanol | 231 g |

The preparation of enteric coated pellets was performed as described in Example 1.

EXAMPLE 3

Formulation with compound 6, according to Table 1. This example gives the composition of one unit dose according to the invention.

| Tablet core | |
|---|---|
| Compound 6, Table 1 | 15 mg |
| Lactose | 119 mg |
| Hydroxypropyl cellulose (low substitution) | 5 mg |
| Hydroxypropyl cellulose (low substitution) | 1 mg |
| Talc | 5 mg |
| Mg(OH)$_2$ | 15 mg |
| Total | 160 mg |

Tablet cores having the composition above and each weighing 160 mg were first made by known techniques.

| | |
|---|---|
| Separating layer (inner) | |
| Hydroxypropyl cellulose | 2 mg |
| Synthetic hydrotalcite [Al$_2$O$_3$.6MgO.CO$_2$.12H$_2$O] | 0.3 mg |
| Separating layer (outer) | |
| Hydroxypropyl cellulose | 2 mg |

The two separating layers were applied to the cores by known coating techniques.

| Enteric coating layer | |
|---|---|
| Hydroxypropyl methylcellulose phthalate | 7 mg |
| Cetyl alcohol | 0.5 mg |

The enteric coating solution was sprayed on the cores coated by the two separating layers by known enteric coating techniques.

We claim:

1. A pharmaceutical preparation comprising:
   (a) an alkaline reacting core comprising an acid-labile pharmaceutically active substance and an alkaline reacting compound different from said active substance, an alkaline salt of an acid labile pharmaceutically active substance, or an alkaline salt of an acid labile pharmaceutically active substance and an alkaline reacting compound different from said active substance;
   (b) an inert subcoating which rapidly dissolves or disintegrates in water disposed on said core region, said subcoating comprising one or more layers comprising materials selected from the group consisting of tablet excipients, film-forming compounds and alkaline compounds; and
   (c) an enteric coating layer surrounding said subcoating layer, wherein the subcoating layer isolates the alkaline reacting core from the enteric coating layer such that the stability of the preparation is enhanced.

2. A preparation according to claim 1, wherein the acid labile compound has the general formula I,

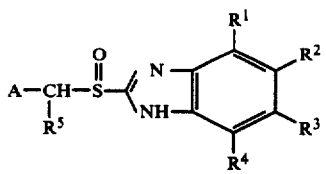

wherein A is an optionally substituted heterocyclic group, $R^1$, $R^2$, $R^3$ and $R^4$ are the same or different and select from among hydrogen, lower alkyl, lower alkoxy, —$CF_3$,

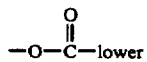

alkyl or halogen and $R^5$ is H or a lower alkyl group wherein "lower" denotes 1-6 carbon atoms except the compound omerprazole, 5-methoxy-2[[(4-methoxy-3,5 dimethyl-2-pyridinyl)methyl]sulfinyl]-1H-benzimidazole; or the acid labile compound is 2-[(2-dimethylaminobenzyl)sulfinyl]-benzimidazole.

3. A preparation according to dlaim 1 wherein the subcoating layer comprises one or more of magnesium oxide, magnesium hydroxide or composite substance [$Al_2O_3.6MgO.CO_2.12H_2O$ or $MgO.Al_2O_3.2SiO_2.nH_2O$], wherein n is not an integer and less than two.

4. A preparation according to claim 2 wherein the subcoating comprises two or more sub-layers.

5. A preparation according to claim 4 wherein the subcoafting comprises hyroxypropyl methylcellulose, hyroxypropyl cellulose or polyvinyl-pyrrolidone.

6. A preparation according to claim 1, wherein an alkaline core comprises the acid labile compound and a pH-buffering alkaline reacting compound which renders to the micro-environment of the acid labile compound a pH of 7-12.

7. A preparation according to claim 6 wherein the alkaline reacting compound comprises one or more of magnesium oxide, hydroxide or carbonate, aluminium hydroxide, aluminium, calcium, sodium or potassium carbonate, phosphate or citrate, the composite aluminium/magnesium compounds $Al_2O_3.6MgO.CO_2.12H_2O$ or $MgO.Al_2O_3.2SiO_2.nH_2O$, wherein n is not an integer and less than two.

8. A preparation according to claim 1, wherein the alkaline core comprises an alkaline salt of the acid labile compound such as the sodium, potassium, magnesium calcium or ammonium salt.

9. A preparation according to claim 7 wherein the alkaline core comprises an alkaline salt of the acid labile compound mixed with an inert, alkaline compound.

10. A preparation according to claim 1, wherein the enteric coating comprises hydroxypropyl methylcellulose phthalate, cellulose acetate phthalate, co-polymerized methacrylic acid/methacrylic acid methyl ester or polyvinyl acetate phthalate, optionally containing a plasticizer.

11. A preparation according to claim 1, wherein the water content of the final dosage form containing the acid labile compound does not exceed 1.5% by weight.

12. Process for the preparation of an oral pharmaceutical formulation containing an acid labile compound in which cores containing the acid labile compound mixed with an alkaline reacting compound or compounds or an alkaline salt of the acid labile compound optionally mixed with an alkaline reacting compound or compounds are coated with one or more inert reacting subcoating layers whereafter the subcoated cores are further coated with an enteric coating layer.

13. A method for the treatment of gastrointestinal disease characterized in that a preparation according to claim 1 is administered to a host in the need of such treatment in a therapeutically effective amount.

14. A preparation according to claim 8, wherein the salt of the acid labile compound is selected from among the sodium, potassium, magnesium, calcium and ammonium salts.

15. A preparation according to claim 1, wherein the subcoating further comprises an alkaline buffering compound.

* * * * *

UNITED STATES PATENT AND TRADEMARK OFFICE
CERTIFICATE OF CORRECTION

PATENT NO. : 4,853,230

DATED : August 1, 1989

INVENTOR(S) : Kurt I. Lovgren; Ake G. Pilbrant, et al.

It is certified that error appears in the above-identified patent and that said Letters Patent is hereby corrected as shown below:

Col. 1, line 24, "neutralto" should read --neutral to--;
Col. 1, line 29, "comounds" should read --compounds--;
Col. 1, line 30, "geneal" should read --general--;
Col. 2, line 23, "Brandstroom" should read --Brandstrom--;
Col. 2, line 24, "Larson" should read --Larsson--;
Col. 2, line 26, "partial" should read --parietal--;
Col. 2, line 35, "exemplifide" should read --exemplified--;
Col. 5, line 41, "controls as the diffusion" should read --controls the diffusion--;
Col. 7, line 33, "$R^6R^7$" should read --$R^6$ and $R^7$--;

Col. 9, line 34, "polyvinylprrollidone" should read --polyvinylprollidone--;
Col. 12, line 39, Example 3, "(low substitution)" should be deleted.
Col. 13, line 34, claim 2, "select" should read --selected--;
Col. 13, line 47, claim 3, "dlaim" should read --claim--;
Col. 14, lines 2+3, claim 5, "hyroxypropyl" should read --hydroxypropyl-- in each instance;

Signed and Sealed this

Twenty-third Day of June, 1992

Attest:

DOUGLAS B. COMER

*Attesting Officer*     *Acting Commissioner of Patents and Trademarks*

UNITED STATES PATENT AND TRADEMARK OFFICE
CERTIFICATE OF CORRECTION

PATENT NO. : 4,853,230
DATED : August 1, 1989
INVENTOR(S) : Kurt I. Lovgren, et al.

It is certified that error appears in the above-indentified patent and that said Letters Patent is hereby corrected as shown below:

Cover page, first column, under "Notice", change "Nov. 22, 2005" to --April 20, 2007--.

Signed and Sealed this

Fifteenth Day of July, 1997

Attest:

BRUCE LEHMAN

*Attesting Officer*   *Commissioner of Patents and Trademarks*